US012213959B2

United States Patent
Ilyasov et al.

(10) Patent No.: US 12,213,959 B2
(45) Date of Patent: Feb. 4, 2025

(54) USE OF 3-O-SULFAMOYLOXY-7β-METHYL-D-HOMO-6-OXAESTRA-1,3,5(10),8(9)-TETRAEN-17A-ONE TO TREAT BREAST CANCER

(71) Applicant: Natalia Eduardovna Iliasova, Saint Petersburg (RU)

(72) Inventors: Shamil Sionovich Ilyasov, Saint Petersburg (RU); Alexandr Grigorievich Shavva, Saint Petersburg (RU); Svetlana Nikolaevna Morozkina, Saint Petersburg (RU)

(*) Notice: Subject to any disclaimer, the term of this patent is extended or adjusted under 35 U.S.C. 154(b) by 833 days.

(21) Appl. No.: 17/292,690

(22) PCT Filed: Sep. 19, 2019

(86) PCT No.: PCT/RU2019/000651
§ 371 (c)(1),
(2) Date: Jan. 28, 2022

(87) PCT Pub. No.: WO2020/096487
PCT Pub. Date: May 14, 2020

(65) Prior Publication Data
US 2022/0160676 A1  May 26, 2022

(30) Foreign Application Priority Data
Nov. 8, 2018 (RU) .......................... RU2018139337

(51) Int. Cl.
*A61K 31/352* (2006.01)
*A61P 35/00* (2006.01)
*C07D 311/78* (2006.01)

(52) U.S. Cl.
CPC ............ *A61K 31/352* (2013.01); *A61P 35/00* (2018.01); *C07D 311/78* (2013.01)

(58) Field of Classification Search
CPC .. A61K 31/352; A61K 31/138; A61K 31/566; A61P 35/00; C07D 311/78; C07J 73/003
See application file for complete search history.

(56) References Cited

FOREIGN PATENT DOCUMENTS

RU    2619457 C1    5/2017
RU    2620084 C1    5/2017

OTHER PUBLICATIONS

Morozkina et al. Synthesis and Some Biological Properties of Sulfamates Derived from 8a-Analogs of Steroidal Estrogens (Russian Journal of Organic Chemistry, vol. 51, 3, 411-416). (Year: 2015).*
International Search Report and Written Opinion (with English translation) issued in corresponding International Patent Application No. PCT/RU2019/000651 dated Jan. 23, 2020 (14 pages).
Morozkina, S.N. Synthesis and Some Biological Properties of Sulfamates Derived from 8α-Analogs of Steroidal Estrogens, Russian Journal of Organic Chemistry, 2015, vol. 51, No. 3, pp. 411-416.
Bubert, Christian et al. 3,17-Disubstituted 2-Alkylestra-1,3,5(10)-trien-3-olDerivatives: Synthesis, In Vitro and In Vivo Anticance rActivity // J. Med.Chem.2007,50,4431-4443.
AstraZeneca. Material Safety Data Sheet. Material name: Tamoxifen Citrate Tablets.

* cited by examiner

*Primary Examiner* — Matthew P Coughlin
*Assistant Examiner* — Meghan C Heasley
(74) *Attorney, Agent, or Firm* — MH2 Technology Law Group, LLP (57) ABSTRACT

The invention relates to the field of medicine and to the chemical and pharmacological industry, and concerns medicaments for the treatment of breast cancer. In particular the invention relates to a use of 3-O-sulfamoyloxy-7β-methyl-D-homo-6-oxaestra-1,3,5 (10),8(9)-tetraen-17a-one as an anti-cancer agent in monotherapy and adjuvant therapy of breast cancer, including the triple negative breast cancer.

15 Claims, 6 Drawing Sheets

USE OF 3-O-SULFAMOYLOXY-7β-METHYL-D-HOMO-6-OXAESTRA-1,3,5(10),8(9)-TETRAEN-17A-ONE TO TREAT BREAST CANCER

TECHNICAL FIELD

The present invention relates to the field of medicine and to the chemical and pharmaceutical industry, and concerns medicaments for the treatment of breast cancer.

BACKGROUND OF THE INVENTION

Breast cancer is the leading oncological disease in women [Parkin D. M., Bray F., Ferlay J., Pisani P., *CA Cancer J. Clin.*, 2005, vol. 55, p. 74-108.]. According to the WHO data, there are 2.09 million patients worldwide with annual breast cancer-related mortality of 627 thousand women every year [http://www.who.int/news-room/fact-sheets/detail/cancer].

A significant portion of tumors with this localization progresses under the action of estrogens [Yue W., Yager J. D., Wang J.-P., Jupe E. R., Santen R. J., *Steroids*, 2013, vol. 78, p. 161-170.]. Immunohistochemical analysis reveals breast cancers that express receptors for estrogen (ERs), progesterone (PRs) and HER2NEU (which renders the cancer "herceptin sensitivity"). A significant portion of tumors have ERs, PRs and/or HER2NEU 3+. If a certain tumor has no ERs and PRs and is not sensitive to Herceptin (ERO, PRO, HER2NEU 0-1), it is considered as a triple negative form (ER−/PR−/HER-2−). This is one of the most lethal forms of breast cancer as it has no targets for the inhibition of its growth. Currently, there are no medicaments for the treatment of this form of cancer in the world.

Estrogens circulate in the blood and accumulate in tumors in the form of sulfates, which are unable to bind to estrogen receptors however after being converted into free hormones they activate tumor growth. Therefore, a promising one is a strategic line of the treatment comprising using inhibitors blocking the formation of this group of free hormones in a tumor.

Tamoxifen is a medicament from the group of selective estrogen receptor modulators, which blocks estrogen effects on hormone-dependent tissues including breast tissue. Tamoxifen is a standard of hormone therapy for premenopausal and postmenopausal women. The most typical side effects which develop during the use of tamoxifen include: an increased risk of venous thrombosis, aggravation of the course of cardiovascular diseases (including angina pectoris attacks), development of endometrial neoplasms (polyps and endometrial cancer), as well as uterine fibroma. Tamoxifen is also hepatotoxic. According to the biopharmaceutical classification system (BCS), developed by Gordon Amidon et al. in 1995, tamoxifen is assigned to the second class, i.e. a medicament with low solubility and high permeability.

Aromatase inhibitors have been shown to be more effective than Tamoxifen. Currently, aromatase inhibitors such as letrozole and anastrazole have been put into use in this field. They are assigned to the first class according to the BCS system, which stands for medicaments with high solubility and high permeability. The side effects of aromatase inhibitors include osteoporosis, hot flashes, and headaches.

In addition to the aforesaid, steroid sulfatase is a subject of great attention due to the local interstitial formation of estrogens from the abundant pool of circulating estrone sulfate. Steroid sulfatase catalyzes the hydrolysis of estrone sulfate to estrone and DHEA sulfate to DHEA (Dibbelt I., *Biol. Chem.*, Hoppe-Seyler, 1991, vol. 372, p. 173-185.; Stein C., *J. Biol. Chem.*, 1989, vol. 264, p. 13865-13872.).

The most known steroid sulfatase inhibitor is EMATE—estrone sulfamate (Ahmed S., *Curr. Med. Chem.*, 2002, vol. 9, no. 2, p. 263-273.). However it has a significant disadvantage. Estrone sulfatase inhibitors containing a sulfamate group cause an irreversible enzyme deactivation with the release of a free ligand [Howarth N. M., Purohit A., Reed M. J. *J. Med. Chem.*, 1994, vol. 37, p. 219-221.]. In particular, estrone sulfamate inhibits estrone sulfatase but the release of free hormone leads to the emergence of strong uterotropic activity [Shields-Botella J. et al., *J. Steroid Biochem. Mol. Biol.*, 2003, vol. 84, p. 327-335.].

A group of estrone sulfatase inhibitors are described in WO9933858 (A2)-1999-07-08, wherein the derivatives of the following general formula can be used as estrone sulfatase inhibitors for the treatment or prevention of estrogen-dependent disorders, such as breast cancer

(I)

These compounds have uterotropic activity as well.

Therefore when searching for new anti-cancer agents it is necessary to take into account that a carrier of the sulfamate group of the estrone sulfatase inhibitor should not possess hormonal activity.

These requirements led to the expansion of the applications of estrogen-based sulphamates in view of their wide range of activity, in particular, their use against recidivist breast cancer [Shah R., et al., Sulfatase inhibitors for recidivist breast cancer treatment: A chemical review, *Eur. J. Med. Chem.*, 2016, vol. 114, p. 170-190.]. In particular, 17α-substituted derivatives of estradiol sulphamate are described.

The prior art also discloses a compound 3,17αβ-disulfamoyloxy-7β-methyl-D-homo-6-oxa-estra-1,3,5(10), 8,14-pentaen of the formula as an inhibitor of the growth of breast cancer cells MCF-7 (RU 2619457, published 16 May 2017). This compound can be selected as the closest prior art to the present invention.

DESCRIPTION

A technical problem of the present invention is to provide compounds and develop an efficient method of synthesis thereof, which compounds can be used as anti-cancer agents in monotherapy and adjuvant therapy of breast cancer, including its most lethal form such as triple negative breast cancer (ER−/PR−/HER-2−).

The problem is solved by providing a use of the compound of formula (2) named 3-O-sulfamoyloxy-7β-methyl-O-homo-6-oxaestra-1,3,5(10),8(9)-tetraen, which inhibits estrone sulfatase as an anti-cancer agent in monotherapy and adjuvant therapy of breast cancer, including the triple negative form (ER−/PR−/HER-2−) of breast cancer.

Below is the scheme for the synthesis of the target compound of formula (2).

(4). The cyclodehydratation reaction of the compound of formula (4) was carried out in hydrochloric acid to give a compound of formula (5). Estratetraen of formula (6) was prepared by hydrogenation of the compound of formula (5) over Pd/C in ethanol, with the yield of 75%. The sulphamate of formula (2) was prepared with the yield of 86%.

The resulting anti-cancer agent belongs to the 5th hazard category ($LD_{50}$>5000 mg/kg). The obtained data allow ranking the doses for the study of antitumour activity as safe. Therapeutically effective doses of the medicament are preferably ranged from 0.1 to 20 mg/kg.

Figure 1:
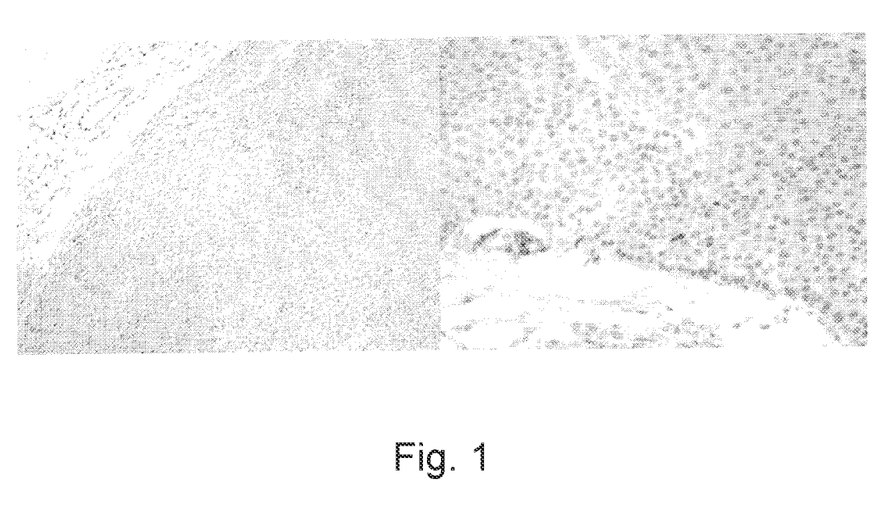
FIG. 1 depicts the staining of breast tumour with ERα antibodies.

Breast tumours (BT) in FBV/N female mice, transgenic for HER-2/neu, are adenocarcinomas which are characterised by a low amount of estrogen receptors (ER) (FIG. 1) and a lack of progesterone receptors (PR). Two adenocarcinoma subtypes can be differentiated, in particular ER+, PR− and ER−, PR−. The immunohistochemical analysis of ERα in breast tumors has revealed single positively stained nuclei only in 10 out of 45 samples (FIG. 1).

Figure 2:
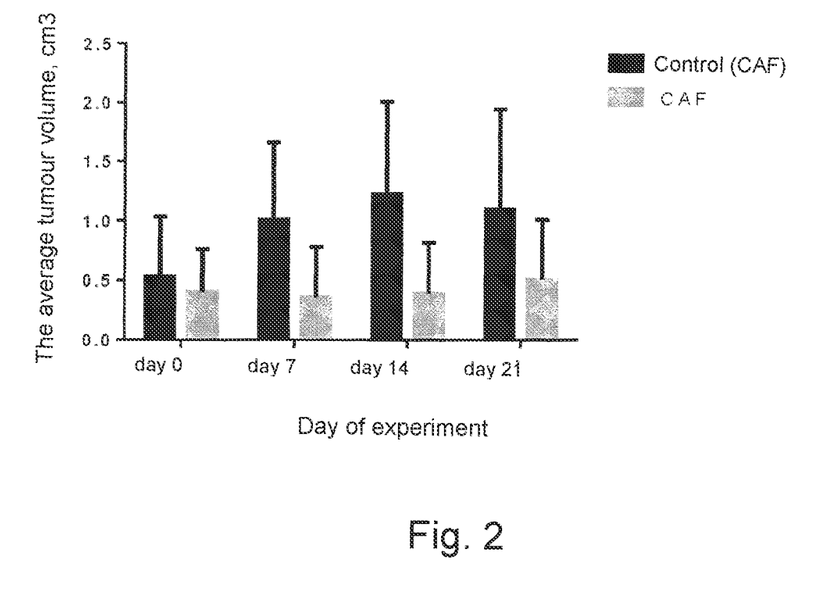
FIG. 2 depicts the average volume of tumours at the beginning of the experiment in mice receiving the CAF therapy.

The model is sensitive to the CAF therapy (cyclophosphamide, adriamycin, 5-fluorouracil) with the observable tumor growth inhibition (TGI) resulting in the stabilization of the average tumor volumes (FIG. 2). The TGI was 63% on Day 14 and 46% on Day 21 of the experiment.

Figure 3:
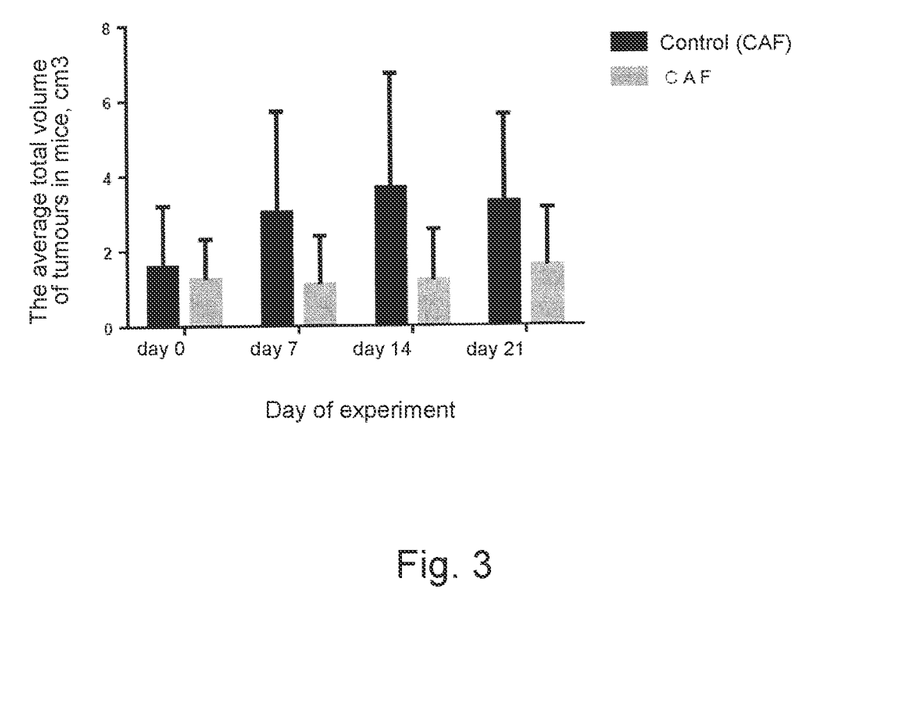
FIG. 3 depicts the average total volume of tumours at the start of the experiment in mice receiving the CAF therapy.
Figure 4:
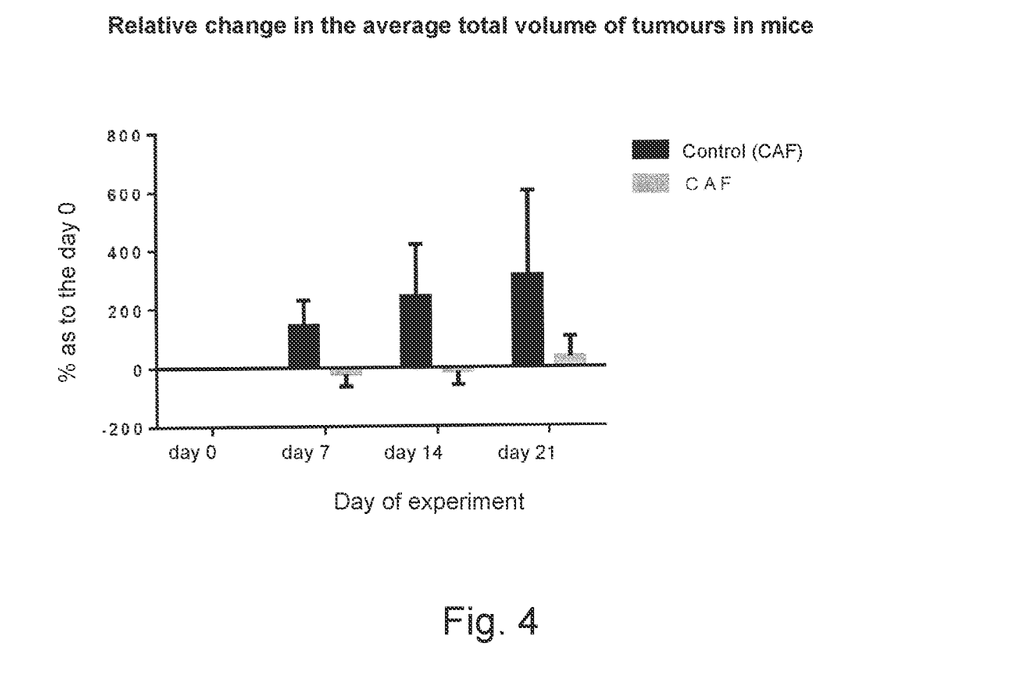
FIG. 4 depicts the relative change in the average total volume of tumours at the start of the experiment in mice receiving the CAF therapy.

As animals may develop multiple tumors, it is considered reasonable to analyze an average total tumor volume in mice The compound of formula (3) was introduced into reaction with vinyl magnesium bromide. The condensation of the resulting vinyl carbinol with 2-methylcyclohexane-1,3-dion resulted in the formation of seco compound of formula (FIG. 3) and its relative change versus tumor volume at the beginning of the experiment (FIG. 4). The graph of the relative increase in tumor volume shows a linear change of this parameter in the control group suggesting that this parameter is appropriate to use for assessing a biological response of tumor to the treatment. For instance the treatment with the CAF therapy does not cause any changes in this parameter for almost 3 weeks indicating disease stabilization.

BRIEF DESCRIPTION OF DRAWINGS

The invention is illustrated by the following figures.

Visualisation: horseradish peroxidase+diaminobenzidine, magn. ×100 (A). A specific staining of cell nuclei of breast duct and nuclei of individual tumour cells (B), magn. ×400.

EXAMPLES

The invention can be further illustrated by examples of the carrying out thereof disclosed herein below.

Example 1

Synthesis of 3-hydroxy-7β-methyl-D-homo-6-oxaestra-1,3,5(10),8(9),8,14-pentaen-17a-one (5)

The secocompound of formula 4 was prepared from 6.0 g of chromanone (3).

To a solution of the secosteroid of formula 4 in 100 ml of methanol, 6 ml of hydrochloric acid was added, and the resulting mixture was boiled for 10 h. The cooled reaction mixture was poured out into cooled water, washed with 5% solution of $NaHCO_3$, followed by water until neutral pH, and dried over $Na_2SO_4$. The solvent was distilled on a rotatory evaporator. The resulting product had a melting point of 237-240° C.

NMR spectrum $^1H$ ($CDCl_3$), ppm: 7.08; 6.45; 6.39; 5.84; 5.30; 5.00 with (1H, C3-OH); 2.79; 2.74-2.40; 2.14, 1.69; 1.28; 1.24 with (3H).

NMR spectrum $^{13}C$ (DMSO-$d^6$), ppm: 214.6; 158.6; 152.6 (C-3, C-5); 137.4; C); 123.9, 125.4; 124.1; 115.7; 118.3; 108.7; 103.8; 69.9; 45.0; 35.4; 28.6; 24.1; 21.1; 18.1.

3-Hydroxy-7β-methyl-D-homo-6-oxaestra-1,3,5 (10),8 (9)-tetraen-17a-one (6) was obtained from 100 mg of estrapentaen. The reaction product was crystallised from MeOH, and dried. 76 mg (75%) of the compound were obtained, T>254° C.

NMR spectrum $^1H$ (DMSO-$d^6$), ppm: 9.44 with (C3-OH); 6.96; 6.33, 6.22; 4.84; 2.80; 2.51; 2.46, 2.18; 2.12; 2.06; 1.91; 1.83; 1.62; 1.52; 1.16, 1.08 with (3H).

NMR spectrum $^{13}C$ (DMSO-$d^6$), ppm: 214.4; 158.1; 152.4; 25 128.2; 122.3; 116.4; 123.8; 108.5; 103.7; 70.5; 46.8; 45.4; 37.0; 29.0; 25.9; 22.3; 21.8; 19.6; 16.4.

The progress of the reactions and individuality of the compounds were checked using thin-layer chromatography (TLC) on the plates Silufol UV254 by Kavalier and Alugram SIL G/UV254 from Machereynagel in the solvent systems hexane/petroleum ether 40-70-ethyl acetate at different ratios. The compounds were detected in ultraviolet light ($\lambda_{max}$=254 nm), by adsorption of iodine vapours or by the reaction with sulfuric acid in methanol (3:1) when heated. The compounds were purified by column chromatography using silica-gel 60 (0.035-0.070 mm; 0.060-0.200 mm) purchased from Acros Organics.

The $^1H$ and $^{13}C$ NMR spectra were recorded in $CDCl_3$ (unless otherwise specified) on the Bruker DPX-300, at the frequencies of 400.130 and 100.613 MHz for $^1H$ and $^{13}C$, respectively, at 298 K. 3-5 mg of the compound solution in 0.6 ml of $CDCl_3$ were used to obtain $^1H$ NMR spectra. $^{13}C$ NMR spectra were obtained in solutions comprising 20-50 mg of the compound in the same volume. Chemical shifts were measured with respect to tetramethylsilane, with the solvent signal ($CDCl_3$/$CHCl_3$=99.9/0.1) having the assigned values of 7.26 ppm ($^1H$) and 77.16 ppm ($^{13}C$).

Example 2

Studying of Pharmacological Activity.

Cell Cultures and Culturing Conditions.

The study analysis was carried out on an passaged MCF-7 human cells culture culture (breast adenocarcinoma). Normal human dermal fibroblasts (HDF) of early passages were used as a negative control.

The cells were cultivated in Carrel vials in DMEM/F12 medium (Biolot) with 1.0% of antibiotic-free fetal bovine embryonic serum (Biolot) added in the 5% $CO_2$ atmosphere, at 37° C.

Evaluation of Proliferative Activity of Cells.

The cells were seeded on Carrel vials at $50 \times 10^4$ cells per flask. To study the proliferative activity of the cells under conditions of sulfatase inhibition, 24 hours after seeding the culture medium was replaced with the medium containing sulfatase inhibitors to a final concentration of 50 μg/ml, and then these tumor cell lines were incubated for various periods of time (24 to 72 hrs). The inhibitor was dissolved in DMSO. The final concentration of DMSO in the culture medium did not exceed 0.5%. To exclude the cytotoxic effect of DMSO, a control sample comprising DMSO without sulfatase inhibitor was prepared.

To exclude nonspecific detrimental effects of the compounds, normal human skin fibroblasts were used. Then the cells were detached with the versene-trypsin solution (Biolot), plated onto Carrel vials containing a fresh complete culture medium. The cells were counted when untreated control cells reached the maximum cell density per unit of surface area of a culture flask (monolayer), and their number was set as 100%. The proliferative activity of all of the studied cell cultures exposed to sulfatase inhibitors was determined in triplicate.

The study of the obtained sulfamate effects on the proliferation of the passaged human MCF-7 cell culture (breast adenocarcinoma) has demonstrated that the steroid of formula 2 at a concentration of 20 μg/ml completely blocks the prolofiration of tumour cells, but it does not influence the growth of human skin fibroblasts having no estrogen receptors. The prolifiration of tumour cells is inhibited to the same extent as under the effect of Tamoxifen, which has been used in clinical practice for more than 30 years. This is very important because sulphamates and Tamoxifen have different mechanisms of action, which makes promising their combined use.

In the experiments on FVB mice, transgenic for HER-2/neu (ER-/PR-/HER2+) having breast tumours, the agent inhibits the proliferation of tumours more effectively than clinically used Tamoxifen, which suggests the potential of their use as a combination for the treatment of breast cancer.

On the MDA-MB-231 cell line of triple negative breast cancer the compound inhibits the cell growth, $IC_{50}=4.8$ μM, which is comparable to Etoposide, a clinically used chemotherapeutic medicament.

Example 3

The study was carried out on female FVB mice transgenic for HER-2/neu of the conventional category, the strain being obtained from the mouse bank Charles River Laboratories (Italy). At the beginning of the study the animals were 21-41 weeks old having weight of 25 to 30 g.

Tamoxifen Hexal (Hexal AG, Germany, 83607 Holzkirchen, lot HA1575 on 01/17) representing a dosage form of the medicament formulated as white or slightly yellowish coated round biconvex tablets, with uniform smooth surface, comprising 20 mg of the active compound was used for the experiment.

The housing conditions were chosen according to the standards specified in The Guide for Care and Use of Laboratory Animals (ILAR publication, 1996, National Academy Press, 1996).

The animals were housed in a separate room in groups (no more than 5 animals in a group) in individual T2 type cages suitable for laboratory rodents. The dimensions of the cages were 268×215×141 mm³ (the base area of 370 cm²) each equipped with a polycarbonate tub, stainless steel lid with a feed container, and divider for drinking bottle.
The cage bedding was made of dust-free wood shavings.

The animals had unrestricted access to the combined complete pelleted feed for laboratory rodents.

Drinking water was given ad libitum in standard 190 ml drinking bottles manufactured by TECNIPLAST, made of high-temperature polysulfone with a silicone ring and a metal lid made of AISI 316 stainless steel.

The room temperature was maintained at a level of 20-26° C. with the relative humidity of 50-70%. The photoperiod was set at 12:12 hrs night/day under artificial lighting with fluorescent lamps.

An identification card was placed on the housing cage with a cage/card number, experimental group number, individual numbers of the animals, their number and sex, study number, name of the responsible researcher. The auricle of each animal was clipped with a metal marker for small laboratory rodents made of Kent-Scientific nickel alloy, USA (markers have three-digit numbers stamped by the manufacturer).

The mice were euthanized with carbon dioxide at the end of the experiment. All animal corpses were autopsied followed by microscopic description.

$LD_{50}$ of the medicament was determined in FVB mice transgenic for HER-2/neu using the OECD 423 test (OECD guideline for testing of chemicals. Acute Oral Toxicity—Acute Toxic Class Method).

12 female mice were used in the experiment.

At the first step, 3 mice were given the medicament at a dose of 300 mg/kg. The study medicament was administered intragastrically (i.g.) using a metal atraumatic gavage (the procedure corresponds to the oral administration in clinical settings). For i.g. administration the active compound of the medicament was mixed with olive oil to prepare the suspension of the required concentration for the administration 0.1 ml of the suspension per 10 g of an animal body weight. The dosage form for the administration was prepared ex tempore.

As no animals died after the administration of the medicament at a dose of 300 mg/kg, the same dose was administered to 3 additional animals. No deaths were detected either. Therefore, the medicament was further administered at the dose of 2000 mg/kg in 2 steps, 3 animals per each step.

The clinical observation and registration of body weight were made according to the scheme as shown in Table 1. The animals were examined 2 times a day, clinically examined individually after the dose administration during the first 60 minutes, with special attention during the first 4 hours, periodically during the first 24 hours, on Day 2 and weekly for up to 14 days. Each animal was thoroughly examined in the housing cage in the observer's hands. The overall conditions of the animals were recorded, such as peculiarities in their behavior, intensity and nature of motor activity, fur and skin appearance.

The body weights of the animals were recorded using a verified high-speed electronic laboratory balance Ohaus Scout Pro (USA) with a maximum load of 2000 g and a measurement step of 0.1 g.

On Day 15, the animals were euthanized and undergone autopsy analysis with the registration of macroscopic changes. The data was collected in a special individual autopsy form.

All of the experimental animals were subject to pathomorphological examination at the end of the study. The euthanized animals were carefully examined for the external pathological changes. The chest and abdominal cavities were examined along with the macroscopic analysis of internal organs. The microscopic analysis of organs and tissues of the laboratory animals was not carried out, because no deaths of the animals were recorded over the whole observation period. In addition, the macroscopic analysis of the internal organs did not reveal any pathological changes.

TABLE 1

Scheme of observation and weighing of animals when assessing acute toxicity

| | Day of experiment (weighing on Day 1 is conducted before the medicament administration) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Indices | X | X | | | | | X | | | | | | | | X |
| Administering medicaments | X | | | | | | | | | | | | | | |

TABLE 1-continued

Scheme of observation and weighing of animals when assessing acute toxicity

| | Day of experiment (weighing on Day 1 is conducted before the medicament administration) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Clinical examination | X | X | | | | | X | | | | | | | X | |
| Euthanizing animals | | | | | | | | | | | | | | | X |

The study medicament was administered i.g. using a metal atraumatic gavage (with the procedure corresponds to the oral route of administration in clinical settings). The medicament was administered in a single daily dose (20 mg/kg of body weight) and 5-fold daily dose of 100 mg/kg of body weight. Ex tempore solutions of the medicament for administration were prepared in olive oil (refined olive oil supplemented with unrefined extra virgin olive oil available under Global Village "Clasico" trademark, lot L:183351116, expiry date 26.04.2020, BAIEO, Spain). The administered volume was 0.1 ml per 10 g of a mouse body weight (0.2 ml of a ready-to-use formulation for a mouse of 20 g). The medicament administration was started 24 hours after the randomization. Duration of the administration course was 27-28 days.

The reference drug, Tamoxifen, was also administered using a metal atraumatic gavage (the procedure corresponds to the oral administration in clinical settings), at a daily dose of 4.0 mg/kg calculated on the basis of the clinical doses [5]. This dose corresponds to a human daily dose of 20 mg/kg. A tamoxifen tablet was crushed in a pounder, and the resulting powder was used to prepare a suspension in 40 ml of the olive oil, the administered volume was 0.08 ml per 10 g of a mouse body weight, the duration of administration was the same as that of the experimental medicament and last for 27-28 days.

The control groups were given the olive oil (placebo).

The evaluation criteria included the clinical observation data, animals body weights, time of death (if applicable), tumor growth over time, pathomorphological examination data (verification of a neoplasm during autopsy, assessment of toxic effects by macroscopic presentation of changes in the internal organs).

Body Weight Measurement

The animals body weights were recorded before the first administration of the medicaments and then twice per week using a verified high-speed electronic laboratory balance Ohaus Scout Pro (USA) with a maximum load of 2000 g and a measurement pitch of 0.1 g.

Tumour Size Measurement

The macroscopically detectable tumor nodes were measured in the animals once per week during the weighing process. Two linear dimensions including the largest one and the largest rectangular to the former were recorded for each of the nodes. The largest dimension was taken as a length (a) and the second dimension as a width (b) of the tumor nodes. A tumor volume was calculated by the expression as follows:

$$V=(a\times b)2/2,$$

The efficacy of the therapy was assessed by recording a change in the average tumor volume, tumor growth inhibition (TGI), and the average total tumor volumes and its change over time in each of the mice.

The percent of tumor growth inhibition was calculated by the expression as follows:

$$TGI=(V_{ctrl}-V_{exp})/V_{ctrl}\times 100(\%),$$

where $V_{ctrl}$ is an average tumor volume in a control group, and $V_{exp}$ is an average tumor volume in an experimental group.

The primary data from individual forms were transferred to Microsoft Excel 2007 books. The group arithmetic average (M) and standard deviation (m) were calculated for all quantitative data. The statistical analysis was performed using the statistical software GraphPad Prism 6.0. The differences between the groups were assessed using ANOVA regression analysis and the Fisher's exact test.

When assessing the acute toxicity the animals were continuously observed for the first 60 minutes, and then examined every hour for 3 hours and further once in 24 hours. On the second day, the observation was carried out twice per day. Further the observations were made once per day. The clinical examination of each of the animals was carried out after the active compound administration, every other day, and then weekly. The animal was thoroughly examined in the housing cage in the observer's hands. The overall conditions of the animals were recorded, such as peculiarities in their behavior, intensity and nature of motor activity, fur and skin appearance.

During the experiment no animals deaths were detected when the medicament was administered at a dose of 300 mg/kg. None of the animals exhibited visual signs of intoxication over the entire observation period. The appearance and behavior of the animals were as usual. When picked up by hands, the animals displayed a conventional weak reaction. No vocalization from the animals was detected upon the administration of the medicament or shortly thereafter.

The daily monitoring of the general condition and behavioral reactions of the animals has shown that a single oral administration of the test medicament did not affect the general condition and activity of the experimental animals exposed to intoxication.

The body weights are shown in Tables 2 and 3.

TABLE 2

Changes in the body weights of the animals upon administration of the medicament at a starting dose of 300 mg/kg

| Dose of | Day of experiment | | | |
|---|---|---|---|---|
| 300 mg/kg | 1 | 2 | 7 | 14 |
| Series 1 | 03.05.2018 | 04.05.2018 | 09.05.2018 | 16.05.2018 |
| Mouse No. 1 | 27.5 | 27.6 | 28.0 | 28.4 |
| Mouse No. 2 | 26.4 | 26.8 | 27.0 | 27.0 |
| Mouse No. 3 | 29.6 | 24.2 | 29.4 | 29.8 |
| Series 2 | 15.05.2018 | 16.05.2018 | 21.05.2018 | 28.05.2018 |
| Mouse No. 4 | 26.0 | 26.5 | 27.4 | 29.3 |

TABLE 2-continued

Changes in the body weights of the animals upon administration of the medicament at a starting dose of 300 mg/kg

| Dose of | Day of experiment | | | |
|---|---|---|---|---|
| 300 mg/kg | 1 | 2 | 7 | 14 |
| Mouse No. 5 | 27.0 | 25.2 | 25.6 | 26.0 |
| Mouse No. 6 | 28.0 | 27.3 | 28.2 | 27.9 |
| Average (% from baseline) | 27.4 | 27.1 (−1) | 27.6 (1) | 28.1 (2) |
| Lethal effects (dead/total) | | | | 0.6 |

TABLE 3

Changes in the body weights of the animals upon administration of the medicament at a dose of 2000 mg/kg

| Dose 2000 | Day of experiment | | | |
|---|---|---|---|---|
| mg/kg | 1 | 2 | 7 | 14 |
| Series 1 | 30.05.2018 | 31.05.2018 | 05.06.2018 | 12.06.2018 |
| Mouse No. 1 | 26.4 | 27.0 | 25.7 | 27.0 |
| Series 1 | 17.09.2018 | 18.09.2018 | 23.09.2018 | 30.09.2018 |
| Mouse No. 2 | 28.4 | 27.9 | 24.7 | 28.3 |
| Mouse No. 3 | 25.0 | 25.5 | 24.5 | 24.9 |
| Series 2 | 15.05.2018 | 16.05.2018 | 21.05.2018 | 28.05.2018 |
| Mouse No. 4 | 26.6 | 26.5 | 25.1 | 26.4 |
| Mouse No. 5 | 24.0 | 25.2 | 25.6 | 26.0 |
| Mouse No. 6 | 26.7 | 27.3 | 28.2 | 27.9 |
| Average (% from baseline) | 26.2 | 26.1 (−1) | 24.7 (−6) | 26.3 (0) |
| Lethal effects (dead/total) | | | | 0.6 |

As follows from the date presented in Table 2, a 1% of the average body weight decrease on Day 2 was attributed to the animals, which were administered with the medicament at a dose of 300 mg/kg.

As no animals died upon administration of a dose of 300 mg/kg, the administration of the medicament was set at a dose of 2000 mg/kg. The medicament was administered in 2 steps with a break of 3 hours in a volume of 0.1 ml per 10 g of a body weight per step at the concentration of 100 mg/ml, because the suspension in oil is thicker at higher concentrations and precludes the medicament to be administered through a gavage. No clinical signs of intoxication were observed after the administration of 2000 mg/kg dose. Regardless of the group the width of the palpebral fissure of the animals was almost unchanged during the entire observation period. No pathological discharges from the eyes were detected. The nose was pink, moderately moist without pathological discharges. The fur of all mice was neat and shiny without bald spots. A 1% decrease of the animals body weight was registered on Day 2 and a 6% weight decrease on Day 7 from the initial weight (Table 3). By the end of the observation period the average body weight did not differ from the initial weight.

On Day 15 the animals were euthanized followed by autopsy analysis. Upon macroscopic analysis no changes of the internal organs were detected.

The autopsy data were as follows:

The fur of the animals had a neat appearance, was shiny without bald spots. The nutritional status of the animals was satisfactory.

There were no pathological discharges from natural orifices.

The submandibular lymph nodes were rounded, pale pink in color, and moderately dense. The salivary glands were of normal shape, pale yellow in color, and moderately dense.

The peritoneum was smooth and shiny without free fluid in the cavity.

The spleen was not enlarged, dense, and the capsule was smooth and shiny. The pancreas was pale pink in color with lobed structure.

The size and shape of the liver were not changed, the liver capsule is shiny. The liver tissue had brownish color and moderately dense texture.

The kidneys were dense, the capsule was smooth, shiny, and there was a moderate outgrowth of adipose tissue around the kidneys.

The ovaries were not enlarged with shiny surface.

The stomach had folded shiny mucous membrane with a small amount of mucus and food contents in the lumen.

The pleura was smooth and shiny without free fluid in the chest cavity. The thymus was triangular in shape, whitish in color. Lungs were light pink in color, airy.

Therefore, according to the OECD 423 test, the medicament can be assigned to the $5^{th}$ or unclassified category with $LD_{50}$ being equal to or more than 5000 mg/kg, which corresponds to the class of low-hazard compounds according to GOST 12.1.007-76.

The animals satisfactorily tolerated the administration of the medicament, no clinical signs of toxicity being observed Animal body weights were increasing throughout the observation period across all of the groups, the gain in body weight being possibly attributed to the increase in the volume of the tumour nodes in the mice (Table 4, 5). The autopsy analysis at the end of the experiment revealed no specific signs of toxic damage to the internal organs.

TABLE 4

Changes in the average body weight of mice (g) when assessing the antitumor activity of the medicament at doses of 20 mg/kg and 100 mg/kg

| Group | Parameter | Jul. 10, 2018 (1) | Jul. 16, 2018 (7) | Jul. 23, 2018 (14) | Jul. 30, 2018 (21) | Aug. 6, 2018 (28) |
|---|---|---|---|---|---|---|
| Control-2 | M | 27.5 | 27.2 | 27.6 | 28.6 | 30.1 |
| (N = 10) | m | 0.5 | 0.5 | 0.5 | 0.7 | 0.8 |
| 20 mg/kg | M | 26.8 | 27.4 | 27.2 | 27.7 | 28.8 |
| (N = 10) | m | 0.5 | 0.6 | 0.6 | 0.8 | 0.9 |
| 100 mg/kg | M | 27.2 | 27.3 | 27.1 | 27.8 | 28.8 |
| (N = 10) | m | 0.4 | 0.6 | 0.6 | 0.6 | 6.8 |
| Date | | Jun. 27, 2018 (1) | Jul. 2, 2018 (6) | Jul. 9, 2018 (13) | Jul. 16, 2018 (20) | Jul. 23, 2018 (27) |

TABLE 4-continued

Changes in the average body weight of mice (g) when assessing the antitumor activity of the medicament at doses of 20 mg/kg and 100 mg/kg

| Group | Parameter | Jul. 10, 2018 (1) | Jul. 16, 2018 (7) | Jul. 23, 2018 (14) | Jul. 30, 2018 (21) | Aug. 6, 2018 (28) |
|---|---|---|---|---|---|---|
| Tamoxifen-1.4 mg/kg (N = 10) | M | 27.7 | 26.5 | 27.3 | 27.5 | 28.2 |
| | m | 0.8 | 0.8 | 0.9 | 0.9 | 1.0 |

TABLE 5

Changes of the average body weight in mice (g) when assessing the antitumour activity of the medicament at a dose of 2.0 mg/kg

| Group | Parameter | Sep. 18, 2018 (1) | Sep. 24, 2018 (7) | Oct. 1, 2018 (14) | Oct. 8, 2018 (21) | Oct. 15, 2018 (28) |
|---|---|---|---|---|---|---|
| Control-3 (N = 10) | M | 31.4 | 31.8 | 33.7 | 35.8 | 36.7 |
| | m | 0.9 | 1.1 | 1.2 | 1.4 | 1.5 |
| Date | | Aug. 21, 2018 (1) | Jul. 27, 2018 (7) | Sep. 3, 2018 (14) | Sep. 10, 2018 (21) | Sep. 17, 2018 (28) |
| 2 mg/kg (N = 9) | M | 30.5 | 30.8 | 32.7 | 32.9 | 35.3 |
| | m | 1.0 | 1.0 | 1.0 | 1.0 | 1.0 |
| Tamoxifen-2.4 mg/kg (N = 9) | M | 31.0 | 32.0 | 32.9 | 32.8 | 34.2 |
| | m | 1.1 | 1.3 | 1.2 | 1.3 | 1.4 |

The data on the changes of the average tumour volume over time for tumours existing at the beginning of the experiment across the Control-1 group, medicament 20 mg/kg group, medicament 100 mg/kg group and Tamoxifen-1 group are presented in FIG. 1, Table 6, and for the Control-3 group, medicament 2.0 mg/kg group and Tamoxifen-2 group in FIG. 2, Table 7.

TABLE 6

Changes of the average volume of tumors ($cm^3$) at the beginning of the experiment when assessing the medicament's antitumor activity at doses of 20.0 mg/kg and 100.0 mg/kg

| Group | Parameter | Jul. 9, 2018 (0) | Jul. 16, 2018 (7) | Jul. 23, 2018 (14) | Jul. 30, 2018 (21) | Aug. 6, 2018 (28) | % of change to the initial value |
|---|---|---|---|---|---|---|---|
| Control-2 (N = 10) | M | 0.08 | 0.13 | 0.28 | 0.43 | 0.61 | 663 |
| | m | 0.01 | 0.02 | 0.04 | 0.05 | 0.08 | |
| 20 mg/kg (N = 10) | M | 0.18 | 0.28 | 0.43 | 0.54 | 0.55 | 206 |
| | m | 0.04 | 0.06 | 0.09 | 0.14 | 0.14 | |
| | TGI, % | −125 | −115 | −54 | −26 | 10 | |
| 100 mg/kg (N = 10) | M | 0.13 | 0.19 | 0.27 | 0.37 | 0.44 | 238 |
| | m | 0.03 | 0.04 | 0.06 | 0.06 | 0.06 | |
| | TGI, % | −63 | −46 | 4 | 14 | 28 | |
| Date | | Jun. 25, 2018 (−1) | Jul. 2, 2018 (6) | Jul. 9, 2018 (13) | Jul. 16, 2018 (20) | Jul. 23, 2018 (27) | — |
| Tamoxifen-1.4 mg/kg (N = 10) | M | 0.23 | 0.26 | 0.3 | 0.47 | 0.58 | 152 |
| | m | 0.07 | 0.07 | 0.07 | 0.1 | 0.11 | |
| | TGI, % | −188 | −100 | −7 | −9 | 5 | |

M is an average value, m is a mean error, N is a number of tumors at the beginning of the treatment included in the analysis. # the control group from the first set of tests.

TABLE 7

Changes of the average volume of tumors (cm³) at the beginning of the experiment when assessing the medicament's antitumor activity at a dose of 2.0 mg/kg

| Group | Parameter | Sep. 17, 2018 (0) | Sep. 24, 2018 (7) | Oct. 1, 2018 (14) | Oct. 8, 18 (21) | Oct. 15, 2018 (28) | % of change to the initial value |
|---|---|---|---|---|---|---|---|
| Control-3 | M | 0.38 | 0.5 | 0.7 | 0.85 | 0.97 | 155 |
| (N = 10) | m | 0.05 | 0.06 | 0.08 | 0.1 | 0.11 | |
| Date | | Aug. 20, 2018 (0) | Aug. 27, 18 (7) | Sep. 3, 2018 (14) | Sep. 10, 2018 (21) | Sep. 17, 2018 (28) | — |
| 2 mg/kg | M | 0.27 | 0.42 | 0.6 | 0.77 | 1.11 | 311 |
| (N = 48) | m | 0.05 | 0.06 | 0.07 | 0.09 | 0.13 | |
| | TGI, % | 29 | 16 | 14 | 9 | -14 | |
| Tamoxifen- | M | 0.29 | 0.46 | 0.65 | 0.75 | 1.27 | 338 |
| 2.4 mg/kg | m | 0.04 | 0.07 | 0.08 | 0.09 | 0.16 | |
| (N = 39) | TGI, % | 24 | 8 | 7 | 12 | -31 | |

In general, it can be concluded that the medicament has no pronounced antitumour effect on this model within the examined dose range (2.0, 20.0 and 100.0 mg/kg) similar to the reference medicament Tamoxifen at a dose of 4.0 mg/kg (the Tamoxifen-1, Tamoxifen-2 groups). For the medicament at the doses of 20 mg/kg and 100 mg/kg, the TGI by the end of observation period on Day 28 was 10 and 28%, respectively in relation to the Control-2 group. As follows from the obtained data (FIG. 1, Table 6, FIG. 2, Table 7), the average tumour volumes in the mice of the medicament 2.0 mg/kg group and Tamoxifen-2 group were 3.4 and 3.6 times grater than those of Control-2 group on experiment Day 0, respectively. Therefore, the comparison of the absolute values of the tumour volumes across those groups appears to be inaccurate because it could affect the subsequent growth rate over time. Therefore it is more accurate to evaluate the relative changes of these parametres (Table 11, Table 12). It should be noted that when assessing the TGI across the Tamoxifen-2 group, the inhibition was observed on Day 7 to 21, and at the end of the experiment the average volume of tumours at the beginning of the treatment exceeded this parameter in the control group by 31%, which might possibly be associated with the development of tumours resistance to the reference medicament during their growth.

When analyzing the frequency of tumour stabilisations and the development of new tumours throughout the observation period (Table 8), it should be noted that the trend has been toward smaller volumes of new tumours as determined at the end of the observation period. Thus, across the Control-2 group this parameter was 0.28±0.09 cm³, and across the medicament 20 mg/kg group and medicament 100 mg/kg group, 0.19±0.04 cm³ and 0.18±0.04 cm³, which is 32% and 36% less than the control (reference) value, respectively. The medicament at a dose of 2.0 mg/kg had no effect on either the frequency of stabilisations or the volume of newly developing tumours.

TABLE 8

Frequency of tumour stabilisations, number and average volume of new tumours, which developed at the end of the experiment, when assessing the antitumour activity of the medicament.

| Group | Number of tumours at initiation of treatment and frequency of their stabilisations | | Absolute number of new tumours | Average volume of new tumours at the end of the observation period | |
|---|---|---|---|---|---|
| Control-2 | 23 | 4% | 22 | M | 0.28 |
| | | | | M | 0.09 |
| 20 mg/kg | 22 | 9% | 22 | M | 0.19 |
| | | | | M | 0.04 |
| 100 mg/kg | 22 | 9% | 19 | M | 0.18 |
| | | | | M | 0.04 |
| Tamoxifen-1,4 mg/kg | 29 | 10% | 21 | M | 0.16 |
| | | | | M | 0.05 |
| Control-3 | 60 | 8% | 25 | M | 0.23 |
| | | | | M | 0.04 |
| 2 mg/kg | 41 | 5% | 30 | M | 0.33 |
| | | | | M | 0.05 |
| Tamoxifen -2, 4 mg/kg | 39 | 3% | 32 | M | 0.20 |
| | | | | M | 0.05 |

The percentage (%) of disease stabilisations is a parameter similar to the RECIST criterion reflecting the frequency of tumours whose volume was not enlarged more than by 20% at the end of the observation period in relation to the volume at the beginning of the treatment.

When analyzing the changes of the average total volume of tumours (FIG. 3, Table 9, FIG. 4, Table 10) similar data were obtained. The medicament at the doses of 20 and 100 mg/kg had an antitumour effect in terms of TGI, which was 12% and 30%, respectively by Day 28.

TABLE 9

Average total volume of tumours (cm³) in mice when assessing the antitumour activity of the medicament at the doses of 20.0 mg/kg and 100.0 mg/kg

| Group | Parameter | Sep. 17, 2018 (0) | Sep. 24, 2018 (7) | Oct. 1, 2018 (14) | Oct. 8, 2018 (21) | Oct. 15, 2018 (28) | % of change to the initial value |
|---|---|---|---|---|---|---|---|
| Control-2 | M | 0.19 | 0.29 | 0.65 | 0.99 | 1.39 | 632 |
| (N = 10) | m | 0.05 | 0.07 | 0.15 | 0.21 | 0.32 | |
| 20 mg/kg | M | 0.41 | 0.62 | 0.94 | 1.18 | 1.22 | 198 |
| | m | 0.1 | 0.15 | 10.23 | 0.34 | 0.34 | |
| (N = 10) | TGI, % | −116 | −114 | −45 | −19 | 12 | |
| 100 mg/kg | M | 0.28 | 0.41 | 0.59 | 0.81 | 0.97* | 246 |
| | m | 0.07 | 0.13 | 0.21 | 0.28 | 0.29 | |
| (N = 10) | TGI, % | −47 | −41 | 9 | 18 | 30 | |
| Date | | Jun. 25, 2018 (−1) | Jul. 2, 2018 (6) | Jul. 9, 2018 (13) | Jul. 16, 2018 (20) | Jul. 23, 2018 (27) | — |
| Tamoxifen-1.4 mg/kg # | M | 0.66 | 10.76 | 0.88 | 1.38 | 1.68 | 155 |
| | m | 0.17 | 0.18 | 0.28 | 0.37 | 0.41 | |
| (N = 10) | TGI, % | −247 | −162 | −35 | −39 | −21 | |

TABLE 10

Average total volume of tumours (cm³) in mice when assessing the antitumour activity of the medicament at a dose of 2.0 mg/kg

| Group | Parameter | Sep. 17, 2018 (0) | Sep. 24, 2018 (7) | Oct. 1, 2018 (14) | Oct. 8, 2018 (21) | Oct. 15, 2018 (28) | % of change to the initial value |
|---|---|---|---|---|---|---|---|
| Control-3 | M | 2.26 | 3.02 | 4.17 | 5.07 | 5.80 | 157 |
| (N = 10) | m | 0.36 | 0.46 | 0.58 | 0.70 | 0.73 | |
| Date | | Aug. 20, 2018 (0) | Jul. 27, 2018 (7) | Sep. 3, 2018 (14) | Sep. 10, 2018 (21) | Sep. 17, 2018 (28) | — |
| 2.0 mg/kg | M | 1.24 | 1.91 | 2.71 | 3.50* | 5.04 | 307 |
| (N = 9) | m | 0.20 | 0.25 | 0.32 | 0.35 | 0.50 | |
| | TGI, % | 45 | 37 | 35 | 31 | 13 | |
| Tamoxifen-2, 4.0 mg/kg | M | 1.26 | 2.01 | 2.84 | 3.23 * | 5.52 | 338 |
| | m | 0.22 | 0.33 | 0.49 | 0.55 | 1.05 | |
| (N = 9) | TGI, % | 44 | 33 | 32 | 36 | 5 | |

Figure 5:
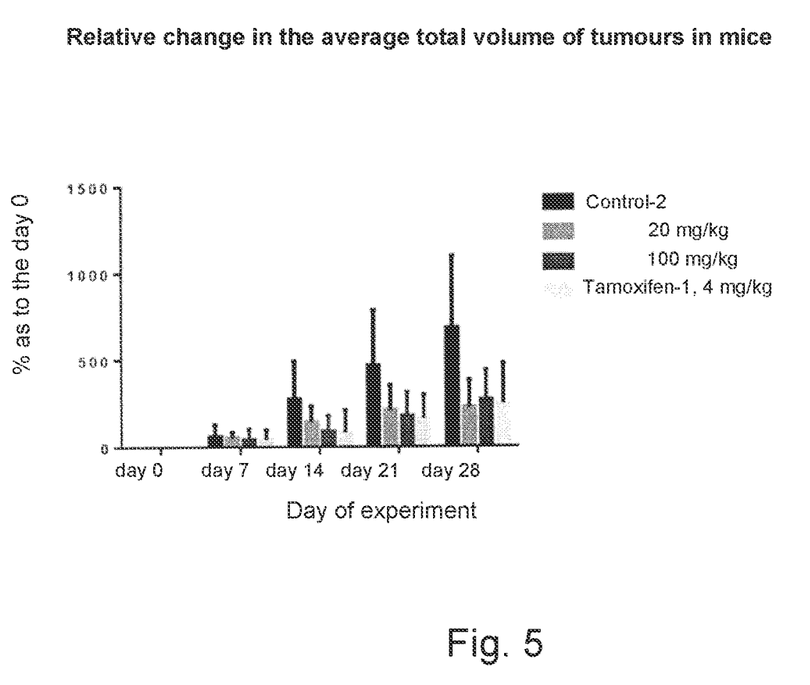
FIG. 5 depicts the relative change in the average total volume of tumours in mice under estimation of antitumour activity of the medicament at the doses of 20 mg/kg and 100 mg/kg.
Figure 6:
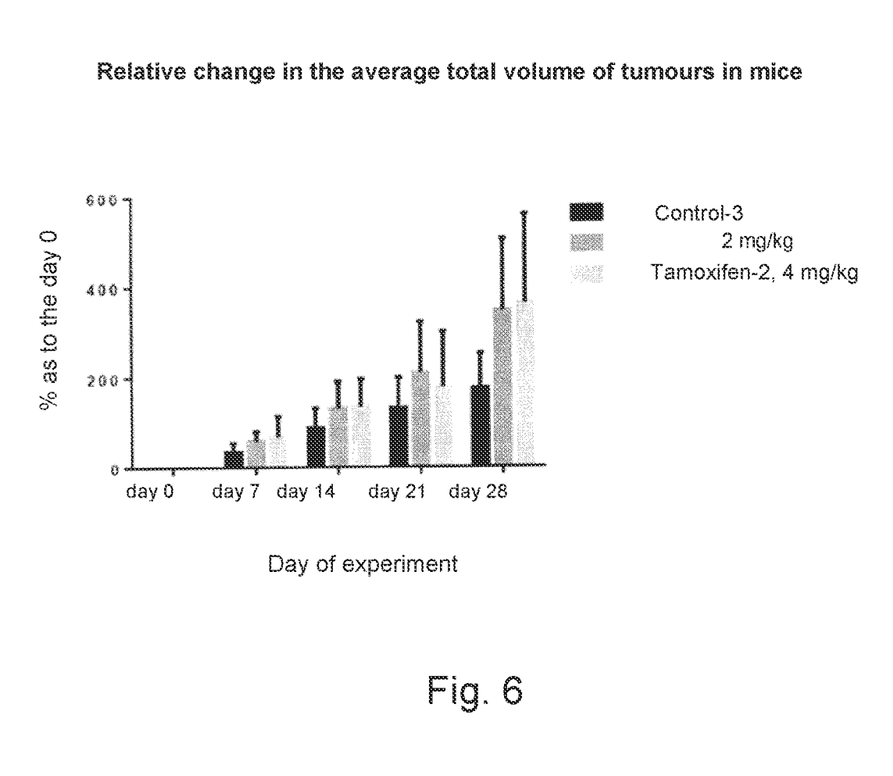
FIG. 6 depicts the relative change of the average total volume of tumours in mice when assessing the antitumour activity of the medicament at a dose of 2.0 mg/kg.

When assessing a relative change in the total volume of tumours in mice, it was established that this parameter varies linearly and constantly increases across the control groups (Control-2, Control-3). Upon administration of the medicament at doses of 20 and 100 mg/kg this parameter was statistically significantly lower for all the experimental groups (FIG. 5, table 11), which confirms that the present medicament under study modulates an effect on the tumour growth, albeit it did not lead to the decrease of the total number of tumors. Upon the administration of the medicament at a dose of 2.0 mg/kg, this parameter was greater than the control values, however it should be noted that this parameter across the Tamoxifen-2 group, exceeded the value across the Control-3 group as well.

TABLE 11

Relative change of the average total volume of tumours to that of Day −1 (expressed in %) in mice when assessing the antitumour activity of the medicament at the doses of 20 mg/kg and 100 mg/kg

| Group | Parameter | Sep. 17, 2018 (0) | Sep. 24, 2018 (7) | Oct. 1, 2018 (14) | Oct. 8, 2018 (21) | Oct. 15, 2018 (28) |
|---|---|---|---|---|---|---|
| Control-2 | M | 0 | 61 | 274 | 467 | 684 |
| (N = 10) | m | 0 | 22 | 69 | 101 | 130 |
| 20.0 mg/kg | M | 0 | 55 | 145 | 209** | 227*** |
| (N = 10) | m | 0 | 9 | 28 | 46 | 49 |
| 100.0 mg/kg | M | 0 | 42 | 89* | 177*** | 269*** |
| (N = 10) | m | 0 | 20 | 29 | 43 | 54 |
| Date | | Jun. 25, 2018 (−1) | Jul. 2, 2018 (6) | Jul. 9, 2018 (13) | Jul. 16, 18 (20) | Jul. 23, 2018 (27) |
| Tamoxifen-1. 4.0 mg/kg # | M | 0 | 40 | 80** | 161*** | 246*** |
| | m | 0 | 18 | 41 | 44 | 73 |
| (N = 10) | | | | | | |

*,,*is $p < 0.05$, $p < 0.01$, $p < 0.001$, respectively, as compared to the control group.

TABLE 12

Relative change of the average total volume of tumours to that of Day −1 (expressed in %) in mice when assessing the antitumour activity of the medicament at the dose of 2.0 mg/kg.

| Group | Parameter | Sep. 17, 2018 (0) | Sep. 24, 2018 (7) | Oct. 1, 2018 (14) | Aug. 15, 2018 (21) | Oct. 15, 2018 (28) |
|---|---|---|---|---|---|---|
| Control-3 | M | 0 | 34 | 88 | 131 | 175 |
| (N = 10) | m | 0 | 6 | 14 | 22 | 25 |
| Date |   | Aug. 20, 2018 (0) | Jul. 27, 2018 (7) | Sep. 3, 2018 (14) | Sep. 10, 2018 (21) | Sep. 17, 2018 (28) |
| 2 mg/kg | M | 0 | 59 | 131 | 210 | 347*** |
| (N = 9) | m | 0 | 7 | 20 | 38 | 53 |
| Tamoxifen- | M | 0 | 67 | 134 | 178 | 363*** |
| 14 mg/kg* | m | 0 | 15 | 21 | 41 | 66 |
| (N = 9) |   |   |   |   |   |   |

\*\*\*is $p < 0.001$, respectively, as compared to the control group.

In terms of all analysed data, the antitumour activity of the medicament on the model of breast tumours in FBV mice, transgenic for HER-2 \neu is not lower than that of the reference durg, Tamoxifen.

The hormonal effects of the medicament on the uterine body was analyzed by comparing the uterine weight without uterine horns at the end of the observation period (Table 13). No statistically significant differences of this parameter as compared to the control group were observed for the medicament administered in the dose range from 2.0 to 100 mg/kg.

TABLE 13

Uterine body weight and body weight of mice with breast tumors during the assessment of the antitumor activity of the medicament

| Group | Uterine weight (MI) | Phase of the estrous cycle (number of mice) | Body weight (g) |
|---|---|---|---|
| Control-2 | 57 ± 7 | E-9 | 30.2 ± 0.9 |
|   | 31 | D-1 | 28.7 |
|   | 53 ± 6 | All | 30.1 ± 0.8 |
| Tamoxifen-2, | 28 ± 1 | E-9 | 34.2 ± 1.4 |
| 4 mg/kg | — | D-0 | — |
|   | 28 ± 1 | All | 34.2 ± 1.4 |
| 2 | 53 ± 3 | E-4 | 35.5 ± 2.5 |
| mg/kg | 24 ± 7 | D-5 | 35.1 ± 1.5 |
|   | 37 ± 6 | All | 35.3 ± 1.1 |
| 20 | 53 ± 4 | E-6 | 29.6 ± 1.5 |
| mg/kg | 45 ± 13 | D-4 | 27.6 ± 0.2 |
|   | 50 ± 4 | All | 28.8 ± 0.9 |
| 100 | 56 ± 5 | E-8 | 28.9 ± 1.0 |
| mg/kg | 34 ± 13 | D-2 | 28.5 ± 0.4 |
|   | 52 ± 5 | All | 28.8 ± 0.8 |

The efficacy of the medicament in terms of TGI tested on a model of multiple breast tumors in FBV/N female mice, transgenic for HER-2/neu was 10% and 28% for the doses of 20 mg/kg and 100 mg/kg, respectively. This activity is similar to that of the reference drug Tamoxifen (4.0 mg/kg), for which the TGI was 5% by the end of the observation period.

It was shown that the present medicament has no uterotropic activity.

According to the OECD 423 test the medicament can be assigned to the 5th or non-classified category with $LD_{50}$ being equal to or more than 5000 mg/kg, which corresponds to the class of low-hazard compounds according to GOST 12.1.007-76.

INDUSTRIAL APPLICABILITY

On animal models with an inoculated human tumour of triple-negative breast cancer, the compound has demonstrated a better action than that of the clinically used Tamoxifen and an aromatase inhibitor Letrozole.

As a result of the conducted experiments the following recommendations for use of the compound have been established:

the monotherapy, and adjuvant therapy for early hormone-positive breast cancer in postmenopausal women, the treatment of triple-negative breast cancer, the monotherapy and adjuvant therapy of breast cancer in postmenopausal women having been treated with Tamoxifen for 2- or 3-years.

the treatment for advanced breast cancer at late stages.

The invention claimed is:

1. A compound, which is 3-O-sulfamoyloxy-7β-methyl-D-homo-6-oxaestra-1,3,5 (10),8 (9)-tetraen-17a-one of formula 2:

2. A method of treating cancer, the method comprising administering to a patient in need thereof an effective amount of 3-O-sulfamoyloxy-7β-methyl-D-homo-6-oxaestra-1,3,5 (10),8 (9)-tetraen-17a-one of formula 2:

3. The method of claim 2, wherein the cancer is a breast cancer.

4. The method of claim 3, wherein the patient is a female patient with an early stage of the breast cancer.

5. The method of claim 3, wherein the patient is a female patient with an advanced form of the breast cancer.

6. The method of claim 5, wherein the patient has been treated with tamoxifen.

7. The method of claim 3, wherein the breast cancer is a triple negative form of the breast cancer.

8. The method of claim 4, wherein the female patient is a woman in postmenopause.

9. The method of claim 5, wherein the female patient is a woman in postmenopause.

10. The method of claim 3, wherein 3-O-sulfamoyloxy-7β-methyl-D-homo-6-oxaestra-1,3,5 (10),8 (9)-tetraen-17a-one of formula 2 is administered as monotherapy or adjuvant therapy.

11. The method of claim 4, wherein 3-O-sulfamoyloxy-7β-methyl-D-homo-6-oxaestra-1,3,5 (10),8 (9)-tetraen-17a-one of formula 2 is administered orally.

12. A method of preparing 3-O-sulfamoyloxy-7β-methyl-D-homo-6-oxaestra-1,3,5 (10),8 (9)-tetraen-17a-one of formula (2), the method comprising the reactions as follows 13. The method of claim 12, wherein the compound of formula (4) is obtained by reacting chromanone of formula (3) with vinyl magnesium bromide and carrying out the condensation of the resulting vinyl carbinol with 2-methyl-cyclohexane-1,3-dione.

14. The method of claim 12, wherein the cyclodehydratation reaction of the compound of formula (4) is carried out in hydrochloric acid in methanol to give a compound of formula (5).

15. The method of claim 12, wherein estratetraen of formula (6) is prepared by hydrogenation of the compound of formula (5) over Pd/C in ethanol.

* * * * *